(12) United States Patent
Feldstein et al.

(10) Patent No.: US 8,460,943 B2
(45) Date of Patent: *Jun. 11, 2013

(54) DETECTION AND MONITORING OF LIVER DAMAGE

(75) Inventors: Ariel E. Feldstein, Highland Heights, OH (US); Anna Wieckowska, Quebec (CA); Nizar Zein, Highland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/979,782

(22) Filed: Dec. 28, 2010

(65) Prior Publication Data

US 2011/0151488 A1 Jun. 23, 2011

Related U.S. Application Data

(63) Continuation of application No. 11/804,505, filed on May 18, 2007, now Pat. No. 7,883,904.

(60) Provisional application No. 60/801,728, filed on May 19, 2006.

(51) Int. Cl.
*G01N 33/566* (2006.01)

(52) U.S. Cl.
CPC ........... *G01N 33/566* (2013.01); *Y10S 436/811* (2013.01)
USPC ........................... 436/501; 435/7.92; 436/811

(58) Field of Classification Search
None
See application file for complete search history.

(56) References Cited

U.S. PATENT DOCUMENTS

| 7,883,904 B2 * | 2/2011 | Feldstein et al. ............. 435/7.92 |
| 2009/0221004 A1 * | 9/2009 | Hong ............................. 435/7.23 |

FOREIGN PATENT DOCUMENTS

| WO | WO 95/31728 A1 | 11/1995 |
| WO | WO 99/16789 | 4/1999 |
| WO | WO 2004/055520 A1 | 7/2004 |
| WO | WO 2005/008242 A1 | 1/2005 |

OTHER PUBLICATIONS

Qi et al., Effects of different peptide fragments derived from proadrenomedullin on gene expression of adrenomedullin gene, Peptides 23 (2002) pp. 1141-1147.*
Bantel, H. et al., "Detection of Apoptotic Caspase Activation in Sera from Patients with Chronic HCV Infection is Associated with Fibrotic Liver Injury", *Hepatology*, vol. 40, No. 5, Nov. 2004, pp. 1078-1087, XP002456078.
Biven, K. et al., "A Novel Assay for discovery and characterization of pro-apoptopic drugs and for monitoring apoptosis in patient sera", *Apoptosis* 2003; 8: 263-268.
Haag, Maria, et al., "A Novel high-through-put assay for screening of pro-apoptotic drugs", *Investigation New Drugs*, 20: 253-259, 2002.
Koelink, Pim J. et al., "Circulating cell death products predict clinical outcome of colorectal cancer patients", BMC Cancer 2009, 9:88.
Kramer, Gero, et al., "Differentiation between cell death modes using measurements of different soluble forms of extracellular cytokeratin 18", Cancer Research 64 1751-1756, Mar. 1, 2004.
Kronenberger, B. et al. "Apoptotic Cytokeratin 18 Neoepitopes in Serum of Patients with Chronic Hepatatis C", *Journal of Viral Hepatitis*, vol. 12, No. 3, May 2005, pp. 307-314, XP002456077.
Luft, Thomas, et al., "Serum Cyokeratin-18 fragments as quantitative markers of epithelial apoptosis in liver and intestinal graft-versus-host disease", Blood, Dec. 15, 2007, vol. 110, No. 13.
Tan, Susanne, et al., "Apoptotic Markers Indicate Nonalcoholic Steatohepatitis in Polycystic Ovary Syndrome", J Clin Endocrinol Metab, Jan. 2010, 95(1):343-348.
Tao, G.-Z, et al., "Monitoring of epithelial cell caspase activation via detection of durable keratin fragment formation", J Pathol 2008: 215: 164-174.
Younossi, Zobair, et al., "A Novel Diagnostic Biomarker Panel for Obesity-related Nonalcoholic Steatohepatitis (NASH)", OBES SURG (2008) 18:1430-1437.
Ueno, T. et al., "Measurement of an apoptotic product in the sera of breast cancer patients", European Journal of Cancer 39 (2003) 769-774.
Wieckowska, A. et al., "In Vivo Assessment of Liver Cell Apoptosis as a Novel Biomarker of Disease Severity in Nonalcoholic Fatty Liver Disease", *Hepatology*, vol. 44, No. 1, Jul. 2006, pp. 27-33, XP002456080.
Wieckowska, A. et al., "Detection of Caspase Activity in the Blood of Patients with Nonalcoholic Fatty Liver Disease as a Novel Biomarker of Disease Severity", *Gastroenterology*, vol. 130, No. 4 Suppl. 2, Apr. 2006, p. A749, XP-008085148 (Abstract Only) (Best Available Copy).
Yilmaz, Y. et al., "Soluble Forms of Extracellular Cytokeratin 18 may Differentiate Simple Steatosis from Nonalocoholic Steatohepatitis", *World Journal of Gastroenterology*, vol. 13, No. 6, Feb. 2007, pp. 837-844, XP008085153.
Bantel, Heike, et al., "Detection of elevated caspase activation and early apoptosis in liver disease", European Journal of Cell Biology 80, 230-239 (Mar. 2001).

* cited by examiner

*Primary Examiner* — Gary W Counts
(74) *Attorney, Agent, or Firm* — Tarolli, Sundheim, Covell & Tummino LLP

(57) ABSTRACT

A method of detecting liver damage in a subject comprises measuring the level of caspase-3 generated cytokeratin-18 fragments in the bodily sample. The level of measuring the level of caspase-3 generated cytokeratin-18 fragments is then correlated with liver disease progression.

18 Claims, 4 Drawing Sheets

DETECTION AND MONITORING OF LIVER DAMAGE

RELATED APPLICATIONS

The present application is a Continuation application of U.S. patent application Ser. No. 11/804,505, filed May 18, 2007, (now U.S. Pat. No. 7,883,904), which claims priority from U.S. Provisional Patent Application Ser. No. 60/801,728, filed May 19, 2006 (now expired), all of which are herein incorporated by reference in their entirety.

FIELD OF THE INVENTION

The present invention relates to a method of detecting or monitoring liver damage and particularly relates to a method of detecting or monitoring liver disease progression in a subject.

BACKGROUND

Nonalcoholic Fatty Liver Disease (NAFLD) is an increasingly recognized form of chronic liver disease affecting both adults and children that may progress to cirrhosis and its feared complications of portal hypertension, liver failure and hepatocellular carcinoma. NAFLD represents a spectrum of conditions ranging form simple accumulation of fat in the liver (steatosis), to steatosis plus hepatocellular injury (steatohepatitis or NASH), to advanced fibrosis and cirrhosis. Simple steatosis is thought to follow a benign non-progressive course, while NASH may lead to cirrhosis in up to 25% of patients. The pathogenesis of NAFLD as it relates to tissue injury and disease progression remains incompletely understood and there is currently no proven effective medication to stop the progression of this disease. At present time, a liver biopsy is the only reliable means to assess the disease severity in NAFLD.

SUMMARY OF THE INVENTION

The present invention relates to a method of assessing the degree of liver damage in a subject. In the method, a bodily sample is obtained from the subject. The level of caspase-3 generated cytokeratin-18 fragments is measured in the bodily sample. The measured level of caspase-3 generated cytokeratin-18 fragments is then correlated with the degree of liver damage in the subject. The correlation of the level of caspase-3 generated cytokeratin-18 fragments with the degree of liver damage can comprise comparing the level of caspase-3 generated cytokeratin-18 fragments with a predetermined value.

In an aspect of the invention, the bodily sample can include a bodily fluid that can be obtained from the subject in a non-invasive or minimally invasive method. The sample of bodily fluid can include at least one of blood, serum, or plasma.

In another aspect of the invention, the level of caspase-3 generated cytokeratin-18 fragments can be measured using an enzyme-linked immunosorbent assay (ELISA). The enzyme-linked immunosorbent assay can measure the level of caspase-3 generated cytokeratin-18 fragments in units per liter (U/L), wherein the higher the U/L of caspase-3 generated cytokeratin-18 fragments in the bodily sample the more severe the liver damage in the subject.

In further aspect of the invention, the liver damage can be associated with nonalcoholic fatty liver disease. The correlation of the level of caspase-3 generated cytokeratin-18 fragments with the degree of liver damage can distinguish steatosis from nonalcoholic steatohepatitis (NASH). Additionally, the correlation of the level of caspase-3 generated cytokeratin-18 fragments with the degree of liver damage can distinguish moderate to severe fibrosis in the subject.

The present invention also relates to a method of assessing the severity of nonalcoholic fatty liver disease in a subject. The method comprises obtaining a bodily sample from the subject. The level of caspase-3 generated cytokeratin-18 fragments in the bodily sample are then measured. The level of caspase-3 generated cytokeratin-18 fragments is correlated with the severity of nonalcoholic fatty liver disease in the subject. The correlation of the level of caspase-3 generated cytokeratin-18 fragments with the severity of liver disease can comprise comparing the level of caspase-3 generated cytokeratin-18 fragments with a predetermined value.

In an aspect of the invention, the bodily sample can be a bodily fluid. The bodily fluid can be obtained from the subject in a non-invasive or minimally invasive method. The sample of bodily fluid can include at least one of blood, serum, or plasma.

In another aspect of the invention, the level of caspase-3 generated cytokeratin fragments can be measured using an enzyme-linked immunosorbent assay (ELISA). The enzyme-linked immunosorbent assay can measure the level of caspase-3 generated cytokeratin-18 fragments in units per liter (U/L), wherein the higher the U/L of caspase-3 generated cytokeratin-18 fragments in the bodily sample the more severe the liver disease in the subject.

In further aspect of the invention, the correlation of the level of caspase-3 generated cytokeratin-18 fragments with the degree of liver damage can distinguish steatosis from nonalcoholic steatohepatitis (NASH). Additionally, the correlation of the level of caspase-3 generated cytokeratin-18 fragments with the degree of liver damage can distinguish moderate to severe fibrosis in the subject.

The present invention also relates to a method of detecting the degree of fibrosis of a liver of a subject. In the method, a bodily sample is obtained from the subject. The level of caspase-3 generated cytokeratin-18 fragments is then measured in the bodily sample. The measured level of caspase-3 generated cytokeratin-18 fragments is then correlated with the degree of fibrosis of the liver of the subject. The correlation of the level of caspase-3 generated cytokeratin-18 fragments with the degree of fibrosis can comprise comparing the level of caspase-3 generated cytokeratin-18 fragments with a predetermined value.

In an aspect of the invention, the bodily sample can include a bodily fluid. The bodily fluid can be obtained from the subject in a non-invasive or minimally invasive method. The sample of bodily fluid can include at least one of blood, serum, or plasma.

In another aspect of the invention, the caspase-3 generated cytokeratin fragments can be measured using an enzyme-linked immunosorbent assay (ELISA). The enzyme-linked immunosorbent assay can measure the level of caspase-3 generated cytokeratin-18 fragments in units per liter (U/L), wherein the higher the U/L of caspase-3 generated cytokeratin-18 fragments in the bodily sample the more severe the fibrosis of the liver of the subject.

The present invention further relates to a method of monitoring the pathogenesis of liver damage caused by an agent administered to a subject. In the method, a bodily sample is obtained from the subject. The level of caspase-3 generated cytokeratin-18 fragments is then measured in the bodily sample. The measured level of caspase-3 generated cytokeratin-18 fragments is then correlated with the degree of liver damage caused by the agent.

The correlation of the level of caspase-3 generated cytokeratin-18 fragments with liver damage can comprise comparing the level of caspase-3 generated cytokeratin-18 fragments with a predetermined value. The predetermined value being can be determined by obtaining a of bodily sample from the subject prior to administration of the agent to the subject and measuring the level of caspase-3 generated cytokeratin-18 fragments in the sample.

In an aspect of the invention, the agent can comprise at least one therapeutic agent selected from the group consisting of HMG CoA reductase inhibitors, COX-2 inhibitors, angiotensin system inhibitor, angiotensin II receptor blocking agents, cytokine inhibitors, tumor necrosis factor-u, (TNF-$\alpha$) inhibitors, antihyperlioproteinemics, inhibitors of cholesterol biosynthesis, insulin sensitizing agents, antihypertensive agents, anti-thrombotic agents, anti-platelet agents, fibrinolytic agents, direct thrombin inhibitors, ACAT inhibitors, CETP inhibitors, V-CAM inhibitors, immunomodulating agents, thiazolidinediones, antioxidants, antiviral agents, anti-apoptotic agents, and glycoprotein receptor inhibitors.

DETAILED DESCRIPTION

Figure 1:
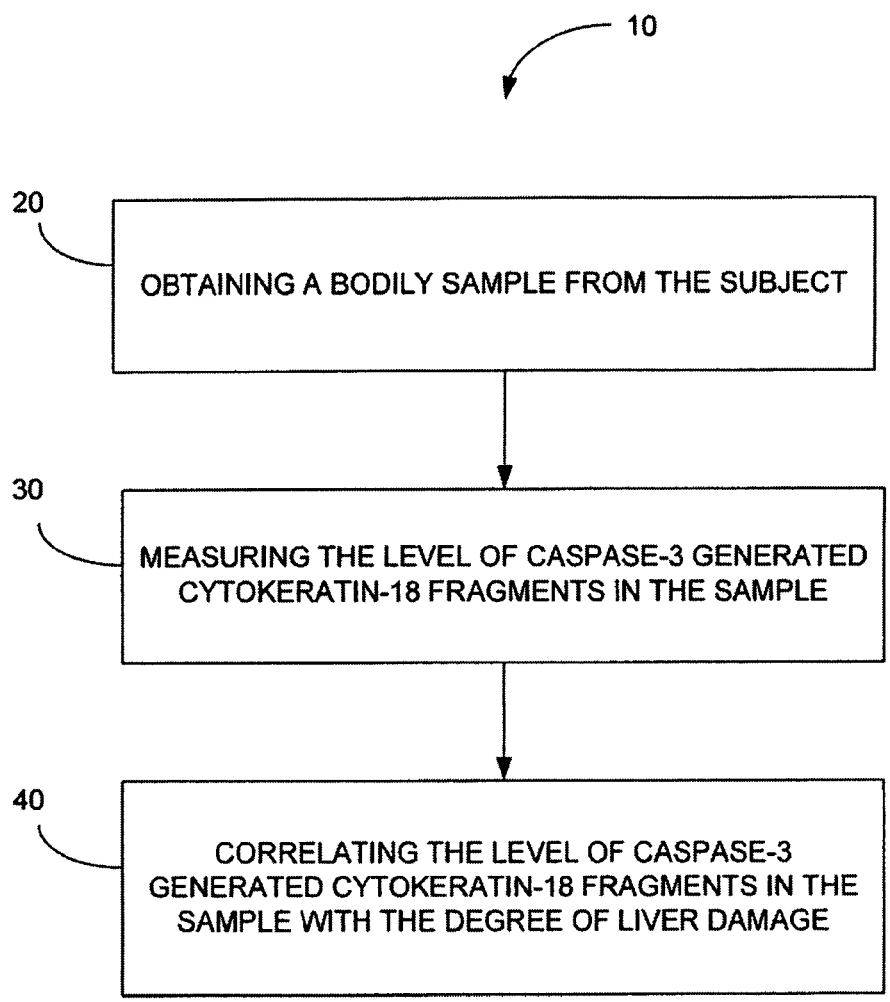
FIG. 1 is a flow diagram of a method in accordance with an aspect of the invention.

All references cited herein are specifically incorporated by reference in their entirety.

The present invention relates generally to a minimally-invasive diagnostic method of detecting, monitoring, or assessing the degree, severity, or progression of liver damage in a subject. The minimally invasive diagnostic method of the present invention in contrast to prior art diagnostic methods is able to readily diagnose liver damage using a bodily sample that is obtained form the subject by non-invasive or minimally invasive methods. The bodily sample can include, for example, bodily fluids, such as blood, serum, or plasma, that are obtained by minimally invasive methods. The liver damage can include, for example, disruption of the architecture of the liver, increase in triglyceride levels, inflammation of the liver, necrotic liver cell death, apoptotic liver cell death, and fibrosis of the liver.

The present invention is based on the discovery that hepatocyte apoptosis is a predictor of the progression of liver disease, and particularly of the progression of nonalcoholic fatty acid liver disease (NAFLD), nonalcoholic steatohepatitis, and liver fibrosis in human subjects. Accordingly, the present invention may be useful as a minimally-invasive diagnostic test to determine liver disease severity in subjects with nonalcoholic fatty liver disease (NAFLD), to distinguish steatosis from non-alcoholic steatohepatitis (NASH), and detect early stages of liver fibrosis.

The present invention also relates to a method for monitoring the response of a subject to treatment of liver disease or liver damage and to a method of monitoring the pathogenesis of liver damage caused by an agent administered to a subject. The present invention may be used to detect or monitor the progression of other forms of liver disease, besides NAFLD, such as Alagille syndrome, $\alpha$-1-antitrypsin deficiency, autoimmune hepatitis, biliary atresia, chronic hepatitis, cancer of the liver, cirrhosis, liver cysts, fatty liver, galactosemia, Gilbert's syndrome, primary biliary cirrhosis, hepatitis A, hepatitis B, hepatitis C, primary sclerosing cholangitis, Reye's syndrome, sarcoidosis, tyrosinemia, type I glycogen storage disease, Wilson's disease, hemochromatosis, and neonatal hepatitis.

In one aspect of the present invention, a method is provided for detecting or assessing the degree of severity of liver damage or liver disease in a subject. The subject may be any human or other animal to be tested for liver damage and/or liver disease progression. The subject may be an "apparently healthy" subject. "Apparently healthy", as used herein, means individuals who have not been previously diagnosed with liver damage, liver disease and/or who have not been previously diagnosed as having any signs or symptoms indicating the presence of liver damage or liver disease. Additionally, apparently healthy subjects may include those individuals having low or no risk for developing liver disease. In addition to apparently healthy subjects, subjects may include individuals having pre-existing liver disease and/or may be at an elevated risk of developing liver damage or liver disease. Subjects having an elevated risk of developing liver damage or liver disease can include, for example, individuals with a family history of liver disease, elevated serum alanine aminotransferase (ALT) and glutamyl-transferase (GGT) activity, hepatitis B surface antigen, hepatitis C virus-RNA positivity, visceral obesity, elevated lipid levels, insulin resistance, hyperglycemia, and hypertension. Subjects at risk of having or developing liver disease, e.g., NAFLD, can also include individuals with elevated liver enzymes and evidence of clinical components of the metabolic syndrome (e.g., any one of obesity, diabetes, hypertension, and hyperlipidemia) in the absence of alternate causes of elevated ALTs.

FIG. 1 illustrates a flow diagram of a method 10 in accordance with one aspect of the invention, of determining or assessing the degree or severity of liver damage and/or liver disease progression in the subject. In the method 10, at 20, a bodily sample is obtained from the subject. The bodily sample can include any bodily sample that can potentially include caspase 3-generated cytokeratin (CK)-18 fragments. The bodily sample may include, for example, tissue and biological fluids from the subject, such as whole blood samples, samples of blood fractions including, but not limited to, serum and plasma. The bodily sample may be fresh blood or stored blood (e.g., in a blood bank) or blood fractions. The sample may be a blood sample expressly obtained for the assays of the present invention, or a blood sample obtained for another purpose, which can be sub-sampled for the assays of the present invention.

Where, for example, the bodily sample is whole blood, the whole blood may be obtained from the subject using standard clinical procedures. Additionally, where the sample is plasma, the plasma may be obtained from whole blood samples by centrifugation of anti-coagulated blood. Such process provides a buffy coat of white cell components and a supernatant of the plasma.

In an aspect of the invention, a bodily sample comprising whole blood may first be taken from the subject and then processed to plasma and stored frozen (e.g., at about −80° C.) until needed for analysis. Alternatively, where the bodily sample is serum, the serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The bodily sample may be pre-treated as necessary by dilution in an appropriate buffer solution, heparinized, concentrated if desired, or fractionated by any number of methods including, but not limited to, ultracentrifugation, fractionation by fast performance liquid chromatography, or other known methods. Any of a number of standard aqueous buffer solutions, employing one of a variety of buffers, such as phosphate, Tris, or the like at a physiological pH can be used.

After obtaining the bodily sample (e.g., blood, serum, plasma), at 30, the level of caspase 3-generated cytokeratin-18 fragments (CK-18 fragments) in the bodily sample is detected, measured, and/or quantifying to determine the level of caspase activity in the subject. CK-18 is cleaved in the liver by caspase. An increase in the level of caspase activity is associated with an increase in hepatocyte apoptosis in the liver. An increase in hepatocyte apoptosis has been shown as one potential marker of liver damage and/or liver disease.

In an aspect of the invention, the caspase-3 generated CK-18 fragments in the bodily sample can be detected and/or quantified using an immunoassay, such as an enzyme-linked immunoabsorbent assay (ELISA). In an ELISA, antibodies specific to a particular antigen are used to detect the presence of, or measure the amount of, a particular molecule. By way of example, an M30-APOPTOSENSE (PEVIVA, Grunwald, Germany) ELISA may be used to detect the presence of, or measure the amount of or level of, caspase 3-generated CK-18 fragments. The APOPTOSENSE assay uses the M30 antibody, which recognizes a neo-epitope in the C-terminal domain of CK-18, which is exposed after cleavage of CK-18 by caspases (e.g., caspase 3) after aspartic acid residue 396. The M30 antibody used in the APOPTOSENSE assay is a mouse monoclonal antibody of the IgG2b subtype.

An ELISA typically comprises the steps of contacting a sample taken from a subject with one or more antibodies, and then assaying for the formation of a complex between the antibody and a protein or peptide in the sample. For ease of detection, the antibody can be attached to a substrate such as a column, plastic dish, matrix, or membrane, such as nitrocellulose. The sample may be untreated, subject to precipitation, fractionation, separation, or purification before combining with the antibody. The APOPTOSENSE assay, for example, is a solid-phase, two-site immunosorbent assay. According to the present invention, bodily samples may be simultaneously reacted with the mouse monoclonal antibody M5 (directed against CK-18 and immobilized to a polystyrene well) and a horseradish peroxidase-conjugated M30 monoclonal antibody. Following the formation of the solid phase/antigen/labeled antibody sandwich, excess unbound conjugate may be removed by a washing step. It should be noted that the APOPTOSENSE assay may also be used in combination with the M65 ELISA (PEVIVA, Grunwald, Germany) which measures total CK-18. Combining the two assays allows the calculation of the relative fraction of CK-18 that is caspase-cleaved.

In an ELISA, interactions between the antibody or antibodies in the sample and the protein(s) or peptide fragment(s) are detected by radiometric, colorimetric, or fluorometric means, size-separation, or precipitation. In one example, detection of the antibody-protein or peptide complex is by addition of a secondary antibody coupled to a detectable tag, such as an enzyme, fluorophore, or chromophore. In the present invention, tetramethyl-benzidine substrate may be added to the assay and color develops in proportion to the bound analyte. The color development may then be stopped and color intensity measured in a microplate reader at 450 nm. By plotting a standard curve from known concentrations versus measured absorbance, the amount of caspase 3-generated CK-18 fragments in the bodily sample can be calculated. The concentration of the CK-18 fragments in the sample can be expressed in Units per Liter (U/L).

It will be appreciated that additional assays can be used to detect and/or quantify caspase 3-generated CK-18 fragments in the bodily sample. These additional assays can include other immunoassays, such as immunoassays employing antibodies disclosed in U.S. Pat. Nos. 6,296,850, 6,716,968, and 6,706,488, all of which are incorporated herein by reference in their entirety. It will also be appreciated that other immunoassays that use CK-18 detecting antibodies can be used to detect the CK-18 fragments. These assays can include radioimmunoassays, both solid and liquid phase, fluorescence-linked assays, and competitive immunoassays as well as other assays, such as mass spectrometry (MS)-based methods (e.g., liquid chromatography MS and electrospray ionization MS). MS based methods may be useful for detecting and/or quantifying the level of caspase 3-generated CK-18 fragments as, for example, the parent molecules, i.e., the non-cleaved CK-18 molecules will have different masses than the caspase 3-generated CK-18 fragments. Additionally, methods such as HPLC may also be useful for detecting the presence of caspase 3-generated CK-18 fragments because distinct parent→daughter ion transitions can occur after cleavage of CK-18 by caspase 3. Thus, charge differences and changes in polarity between cleaved and non-cleaved CK-18 proteins have a high likelihood of showing distinct retention times on HPLC At 40, the assayed level of caspase 3-generated CK-18 fragments can be correlated with liver damage and/or liver disease progression by comparing the level hepatocyte apoptosis with a predetermined value. In one aspect of the invention, the predetermined value can be based upon the level of Ck-18 fragments (e.g., U/L) in comparable samples obtained from the general population or from a select population of human subjects. For example, the select population may be comprised of apparently healthy subjects. In other words, such individuals, if examined by a medical professional, would be characterized as healthy and free of symptoms of liver disease.

The predetermined value can be related to the value used to characterize the level of CK-18 fragments in a bodily sample obtained from a subject. Thus, if the level CK-18 fragments is an absolute value, such as the units per liter of CK-18 fragment in plasma, the predetermined value is also based upon the units per liter of CK-18 fragments in plasma in the general population or a select population of human subjects. Similarly, if the level of CK-18 fragments is a representative value such as an arbitrary unit obtained by a radioimmunoassay, for example, the predetermined value is also based on the representative value.

The predetermined value can take a variety of forms. The predetermined value can be a single cut-off value, such as a median or mean. The predetermined value can be established based upon comparative groups such as the level of CK-18 fragments in one defined group being double the level of systemic marker in another defined group. The predetermined value can be a range, for example, where the general population is divided equally (or unequally) into groups, or into quadrants, the lowest quadrant being individuals with the lowest levels of CK-18 fragments, and the highest quadrant being the individuals with the highest levels of CK-18 fragments.

The predetermined value can be derived by determining the level of CK-18 fragments in the general population. Alternatively, the predetermined value can be derived by determining the level of CK-18 fragments in a select population, such as an apparently healthy population. For example, an apparently healthy, non-viscerally obese population may have a different normal range of CK-18 fragments than will a viscerally obese population or a population otherwise at high risk for NASH. Accordingly, the predetermined values selected may take into account the category in which an individual falls. Appropriate ranges and categories can be selected with no more than routine experimentation by those of ordinary skill in the art.

Predetermined values of CK-18 fragments, such as mean levels, median levels, or "cut-off" levels, for example, may be established by assaying a large sample of individuals in the general or a select population using a statistical model, such as the predictive value method for selecting a positivity criterion or receiver operator characteristic curve, that defines optimum specificity (highest true negative rate) and sensitivity (highest true positive rate) as described in Knapp, R. G., and Miller, M. C. (1992). *Clinical Epidemiology and Biostatistics*. William and Wilkins, Harual Publishing Co., Malvern, Pa.

According to the present invention, the presence or absence of liver damage and/or liver disease in a subject may be determined by comparing a predetermined value of CK-18 fragments, for example, to the level of CK-18 fragments in a bodily sample taken from a subject. A predetermined value of caspase 3-generated CK-18 fragments may first be assayed from a bodily sample taken from an apparently healthy subject or population of apparently healthy subjects (as described above). Where the predetermined value comprises the level of caspase 3-generated CK-18 fragments in U/L, the predetermined value may be within a range of values, such as between about 68 U/L to about 3000 U/L. For example, the predetermined value of CK-18 fragments of healthy controls can be up to about 190 U/L (e.g., about 126 U/L to about 190 U/L, or about 150 U/L).

After determining the predetermined value, a bodily sample may be obtained from a subject at risk for, or suspected of having, liver damage and/or liver disease. The bodily sample may be obtained and then be assayed for the level of caspase 3-generated CK-18 fragments. The predetermined value may be compared to the level of caspase 3-generated CK-18 fragments in the bodily sample. Where the level of caspase 3-generated CK-18 fragments in U/L is substatially higher than the predetermined value (e.g., the measured level is greater than about 200 U/L), it is likely that the subject has a form of liver disease, e.g., steatosis or NASH. Alternatively, where the level of caspase 3-generated CK-18 fragments in the bodily sample is within a range of about 240 U/L to about 991 U/L, it will also be likely that the subject has NASH. If the level of caspase 3-generated CK-18 fragments in the bodily sample is less than about 240 U/L, then the subject is not likely to have a diagnosis of NASH.

According to the present invention, it may also be possible to differentiate between diseases states based upon the predetermined value and level of caspase 3-generated CK-18 fragments in the bodily sample. In one example, steatosis can be differentiated from NASH by measuring the level of CK-18 fragments in a bodily sample obtained from a subject. A measured level of caspase 3-generated CK-18 fragments of about 202 U/L, or a level of caspase 3-generated CK-18 fragments between about 160 U/L and about 217 U/L, would likely indicate the presence of steatosis in a subject, whereas a level of caspase 3-generated CK-18 fragments between about 246 U/L and about 991 U/L (e.g., about 380 U/L) would likely indicate the presence of NASH in a subject. Further, it may also be possible to differentiate one particular type of liver disease, such as NASH, from other types of liver diseases, such as those listed above, by comparing the level of caspase 3-generated CK-18 fragments in a bodily sample with known or predetermined values of caspase 3-generated CK-18 fragments that are characteristic of other types of liver diseases.

In another example, mild liver fibrosis of a subject can be distinguished from moderate to severe liver fibrosis by measuring the level of CK-18 fragments in a bodily sample obtained from a subject. A measured level of caspase 3-generated CK-18 fragments of about 207 U/L, or a level of caspase 3-generated CK-18 fragments between about 160 U/L and about 217 U/L, would likely indicate the presence of mild fibrosis of the liver of a subject, whereas a level of caspase 3-generated CK-18 fragments between about 250 U/L and about 991 U/L (e.g., about 357 U/L) would likely indicate the presence of moderate to severe liver fibrosis in a subject.

Additionally, a predetermined value of CK-18 fragments may be compared to the level of CK-18 fragments in a subject to determine the progression of liver disease in a subject. The extent of the difference between the level of CK-18 in the subject and the predetermined value may also be useful for characterizing the extent of liver damage and/or liver disease progression. For example, a predetermined value comprising the level of caspase 3-generated CK-18 fragments may be derived from an apparently healthy subject or population of apparently healthy subjects (as described above). The predetermined value may be about 234 U/L or, alternatively, may be within a range of about 197 U/L to about 289 U/L. A first bodily sample may then be obtained from a subject at risk for, or known to have, liver disease and then assayed for the level of caspase 3-generated CK-18 fragments (as described above). At least one other bodily sample may then be obtained and subsequently assayed for the level of caspase 3-generated CK-18 fragments. The level of caspase 3-generated CK-18 fragments for each of the bodily samples may then be compared to the predetermined value. Increasing levels of caspase 3-generated CK-18 fragments in the bodily samples will likely indicate a progression of liver disease from a normal state (e.g., caspase 3-generated CK-18 fragment levels of about 215 U/L) or steatosis (e.g., caspase 3-generated CK-18 fragment levels of about 202 U/L) to a diseased state (e.g., caspase 3-generated CK-18 fragment levels of about 395 U/L), such as NASH.

It will be appreciated that incremental changes in the level of caspase 3-generated CK-18 fragments over time may be used to determine the progression of liver disease in a subject. In one example, an incremental increase in the level of caspase 3-generated CK-18 fragments, for example, by about 50 U/L may increase the likelihood that a subject has NASH by about 70% to about 90% (e.g., about 74%). In another example, an incremental increase in the level of caspase 3-generated CK-18 fragments, for example, by about 50 U/L may increase the likelihood that a subject has fibrosis by about 10% to about 20% (e.g., about 18%).

In another aspect of the invention, a method is provided for monitoring the response to treatment of liver disease in a subject. According to the invention, the level of caspase 3-generated CK-18 fragments in the subject is assayed and the assayed level of hepatocyte apoptosis is correlated to liver disease progression in the subject. In one method, a subject having liver disease can be identified. The subject can be identified as having liver disease using, for example, known radiological or biopsy techniques. Optionally, the subject can be identified as having liver disease by obtaining at least one bodily sample from the subject. For example, a bodily sample comprising blood may be obtained from the subject and then processed to plasma. The bodily sample may then be assayed for the level of caspase 3-generated CK-18 fragments, as described above. The level of caspase 3-generated CK-18 fragments will comprise the predetermined value. If the level of caspase 3-generated CK-18 fragments is about 395 U/L, or is between about 380 U/L and 991 U/L, then the subject may be diagnosed as having NASH, for example.

At least one treatment modality may be administered to the subject before or after detection of liver damage and/or liver disease. An example of a treatment modality may include a weight loss program comprising, for example, a regimen of dieting and exercise. Treatment modality can also include a therapeutic agent that is administered to the subject for treating liver damage and/or liver disease. Such therapeutic agents can include, for example, metformin (e.g., Glucophage XR, Bristol Myers Squibb, Princeton, N.J.) and ppar-gamma agonists (e.g., pioglitizaone).

After at least one therapeutic modality has been administered, a bodily sample can be obtained from the subject and then assayed to determine the level of caspase 3-generated CK-18 fragments (as described above). After the level of caspase 3-generated CK-18 fragments in the bodily sample has been determined, this level may then be compared to a predetermined value, such as level of caspase 3-generated CK-18 fragments in a bodily sample obtained from the subject prior to administration of the treatment modality. If the level of caspase 3-generated CK-18 fragments in the sample is lower than the predetermined value, then the therapeutic modality has likely provided a therapeutic effect against liver damage and/or liver disease. Alternatively, if the level of caspase 3-generated CK-18 fragments in the sample is higher than the predetermined value, then the therapeutic modality has likely not provided a therapeutic effect against liver disease.

The extent of the difference between the predetermined value and the level of caspase 3-generated CK-18 fragments in the bodily sample may also be useful for characterizing the extent of the effect of the therapeutic modality and, thus, may be used to determine and monitor an effective treatment strategy with the therapeutic modality. The extent of the difference between the predetermined value and the level of caspase 3-generated CK-18 fragments in the bodily may also be useful for determining if and when therapeutic modalities, which are targeted at treating disorders where hepatocyte apoptosis is linked to the pathogenesis of the disorder, should and should not be prescribed for a subject. For example, subjects with levels of caspase 3-generated CK-18 fragments above a certain cutoff value, or that are in the higher tertile or quartile of a "normal range," could be identified as those in need of more aggressive intervention with therapeutic modalities.

In addition to monitoring the response of a subject with liver damage and/or liver disease to a treatment, it may also be useful to determine an effective amount of an agent, such as the therapeutic agents, for treating liver damage and/or liver disease where hepatic apoptosis is linked to pathogenesis of a particular disease. By monitoring the level of caspase 3-generated CK-18 fragments in a subject during or following administration of a therapeutic agent, an effective amount of the therapeutic agent can be determined.

An effective amount of a therapeutic agent may include a dosage sufficient to provide a medically desirable result in a subject having a particular disease or condition. The effective amount will vary with the particular disease or condition being treated, the age and physical condition of the subject being treated, the severity of the condition, the duration of the treatment, the nature of any concurrent therapy, the specific route of administration, and the like factors within the knowledge and expertise of the health practitioner. For example, an effective amount can depend upon the degree to which an individual has abnormally elevated levels of caspase 3-generated CK-18 fragments. Alternatively, an effective amount can be that amount which decreases the levels of in the level of caspase 3-generated CK-18 fragments. It will be recognized that when the therapeutic agent is used in acute circumstances, it can be used to prevent one or more medically undesirable results that typically flow from such adverse events. It is expected that dosages will range depending on the method of administration. In the event that a response in a subject is insufficient at the initial dosages applied, higher dosages (or effectively higher dosages by a different, more localized delivery route) may be employed to the extent that patient tolerance permits. Multiple dosages per day are contemplated to achieve appropriate systemic levels of the therapeutic agent.

In yet another aspect of the invention, a method is provided for monitoring the pathogenesis of liver injury caused by an agent administered to a subject. The method includes assaying the level of in the level of caspase 3-generated CK-18 fragments in a subject and then correlating the level of caspase 3-generated CK-18 fragments with the extent of the liver damage or liver injury. In one aspect of the invention, a subject may be identified as described above. For example, the subject may be an apparently healthy subject or, alternatively, a subject having liver disease or being at risk of having liver disease. After the subject is identified, the level of in the level of caspase 3-generated CK-18 fragments in the subject may be assayed by, for example, obtaining a bodily sample from the subject and then assaying the bodily sample to determine a caspase activity. The level of caspase activity may be determined by determining or quantifying the level of caspase 3-generated CK-18 fragments in the bodily sample.

At least one agent may be administered to the subject before or after determination of the level of hepatocyte apoptosis. The agent can include any one or combination of the therapeutic agents. For example, the agent may include any type of prescription or over-the-counter drug or medication.

Examples of prescription or over-the-counter medications may include, but are not limited to ppar-gamma agonists, antioxidants, antiviral agents, HMG CoA reductase inhibitors, COX-2 inhibitors, angiotensin system inhibitors, angiotensin II receptor blocking agents, cytokine inhibitors, tumor necrosis factor-α (TNF-α) inhibitors, anti-hyperlipoproteinemics, inhibitors of cholesterol biosynthesis, insulin sensitizing agents, anti-hypertensive agents, anti-thrombotic agents, anti-platelet agents, fibrinolytic agents, direct thrombin inhibitors, ACAT inhibitors, CETP inhibitors, V-CAM inhibitors, immunomodulating agents, thiazolidinediones, antioxidants, anti-viral agents, anti-apoptotic agents, and glycoprotein receptor inhibitors.

Examples of insulin sensitizing agents include, without limitation, ppar-gamma agonists or thiazolidinediones, such as rosiglitazone (Avandia) and pioglitazone (Actos), and metformin (Glucophage).

Examples of antioxidants include vitamins, such as Vitamins A, C and E; vitamin cofactors and minerals such as coenzyme A, coenzyme Q10, selenium zinc, and manganese; hormones (e.g., melatonin); carotenoid terpenoids such as lycopene, lutein, α-carotene, β-carotene, zeaxanthin, and astaxanthin; non-carotenoid terpenoids (e.g., eugenol); flavonoid polyphenolics such as flavonols (e.g., resveratrol, pterostilbene, kaempferol, myricetin, isorhamnetin, and proanthocyanidins), flavones (e.g., quercetin, luteolin, apigenin, and tangeritin), flavanones (e.g., hesperetin, naringenin, and eriodictyol), flavan-3-ols (e.g., catechin, gallocatechin, epicatechin, epigallocatechin, theaflavin, and thearubigins), and isoflavone phytoestrogens (e.g., genistein, daidzein, and glycitein); phenolic acids and their esters (e.g., ellagic acid, gallic acid, salicylic acid, rosmarininc acid, cinnamic acid, chlorogenic acid, chicoric acid, gallotannins, and ellagitannins); other organic antioxidants such as citric acid, lignan, oxalic acid, phytic acid, uric acid, R-α-lipoic acid, silymarin, and N-acetylcysteine; and other antioxidants such as choline and choline derivatives.

Examples of antiviral agents include acyclic nucleosides such as acyclovir or ganciclovir, interferons such as α-, β- or γ-interferon, reverse transcriptase inhibitors and nucleosides, transport inhibitors such as dipyridamole, 2',3'-dideoxynucleosides (including β-L-FddC), 2,3'-dideoxy-2',3'-didehydronucleosides (including β-L-Fd4C), 3TC (lamivudine), AZT, 2',3'-dideoxycytidine, 2',3'-dideoxyadenosine, 2',3'-dideoxyinosine, 2',3'-dideoxythymidine, 2',3'-dideoxy-2',3'-didehydrothymidine and 2',3'-dideoxy-2',3'-didehydrocytidine, tenofirir DF, adefovir, dipivoxil, immunomodulators such as interleukin II and granulocyte macrophage-colony stimulating factor, erythropoetin, ampligen, thymodulin, thymopentin, foscarnet, ribavirin and inhibitors of HIV binding to CD4 receptors, e.g., soluble CD4, CD4 fragments, CD4 hybrid molecules, glycosylation inhibitors such as 2-deoxy-D-glucose, castanospermine, and 1-deoxynojirimycin.

Examples of anti-apoptotic agents include Bcl-2 family proteins, NMDA, caspase inhibitors, p53 inhibitors, hematopoietic growth factors, Thalidomide, anti-TNF-α antibodies, FADD-like proteins, anti-FasL antibodies, and anti-CD40 antibodies.

Anti-thrombotic and/or fibrinolytic agents include, but are not limited to, plasminogen (to plasmin via interactions of prekallikrein, kininogens, Factors XII, XIIIa, plasminogen proactivator, and tissue plasminogen activator (TPA); streptokinase; urokinase (UK); anisoylated plasminogen-streptokinase activator complex; pro-urokinase (pro-UK); rTPA (alteplase or activase; r denotes recombinant); rpro-UK; abbokinase; eminase; sreptase anagrelide hydrochloride; bivalirudin; dalteparin sodium; danaparoid sodium; dazoxiben hydrochloride; efegatran sulfate; enoxaparin sodium; ifetroban; ifetroban sodium; tinzaparin sodium; retaplase; trifenagrel; warfarin; and dextrans.

Lipid-reducing agents include, but are not limited to, gemfibrozil, cholystyramine, colestipol, nicotinic acid, ursodeoxycholic acid, probucol lovastatin, fluvastatin, simvastatin, atorvastatin, pravastatin, cerivastatin, and other HMG-CoA reductase inhibitors.

Direct thrombin inhibitors include, but are not limited to, hirudin, hirugen, hirulog, agatroban, PPACK, and thrombin aptamers.

Glycoprotein IIb/IIIa receptor inhibitors may be antibodies and non-antibodies, and include, but are not limited to, ReoPro (abcixamab), lamifiban, and tirofiban.

Examples of COX-2 inhibitors include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1, 2-3-thiadiazoles as anti-inflammatory agents"; U.S. Pat. No. 5,691,374 "Diaryl-5-oxygenated-2-(SH)-furanones as COX-2 inhibitors"; U.S. Pat. No. 5,698,584 "3,4-diaryl-2-hydroxy-2,5-d-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789, 413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^{+in}$ plasma tend to activate the system, while factors that increase these parameters tend to suppress its function.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists.

Examples of angiotensin II antagonists include: peptidic compounds (e.g., -saralasin, [(San$^1$)(Val$^5$)(Ala$^8$)]angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (3S, 4S)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, Pa.); Losartan (DUP7531MK954, DuPont Merck Pharmaceutical Company); Remikirin (RO42-5892, F. Hoffman LaRoche AG); $A_2$ agonists (Marion Merrill Dow) and certain non-peptide heterocycles (G. D. Searle and Company). Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

After administration of the therapeutic agent, a bodily sample can be obtained from the subject and then assayed for the level of caspase 3-generated CK-18 fragments (as described above). The level of caspase 3-generated CK-18 fragments of the second sample can then be compared with the level of caspase 3-generated CK-18 fragments to determine whether there is a correlation between administration of the agent and liver injury. If the level of caspase 3-generated CK-18 fragments in the second sample is increased when compared to the predetermined value, then it is likely that the agent is the cause of the liver injury. Alternatively, where there is little or no difference between the level of caspase 3-generated CK-18 fragments in the second sample and the predetermined value, then it is not likely that the agent is the cause of the liver injury.

The following example is for the purpose of illustration only and is not intended to limit the scope of the claims, which are appended hereto.

EXAMPLE 1

The objective of the current study was to determine the clinical utility of quantifying hepatocyte apoptosis in human NAFLD through a novel noninvasive blood test by comparing the results to the traditional histological evaluation.

Patients and Methods

Patient Characteristics:

The study was approved by the Cleveland Clinic Institutional Review Board, and all patients gave written informed consent prior to participation. Our cohort consisted of 44 consecutive patients undergoing a liver biopsy for a clinical suspicion of NAFLD by their treating hepatologist. All had persistently elevated liver enzymes (for more than 3 months) and evidence of clinical components of the metabolic syndrome (any of the following: obesity, diabetes, hypertension, hyperlipidemia) in the absence of alternate causes of elevated aminotransferases. Patients were excluded if alcohol consumption was >30 g/day for males and >20 g/day for females and if other liver diseases were detected by serologic testing and imaging studies. Blood was obtained from each patient at the time of liver biopsy. Demographic, clinical and laboratory data were collected. Two patients were excluded due to an alternative diagnosis on liver histology (necrosis and hepatocyte dropout of unknown etiology and primary biliary cirrhosis) and one due to hemolysed blood sample. Patients were subsequently divided into 4 groups according to their histologic findings (see Liver histology below): normal biopsy, "not NASH" (simple fatty liver), "borderline NASH" and "definitive NASH". Subjects with "borderline NASH" (n=2) were not included in the analysis, as according to Kleiner et al., these patients could not be classified into a clear-cut category. A total of 39 patients with clinically suspected NAFLD were used to perform the final statistical analysis. In addition, 35 healthy age-matched controls from blood bank donors without clinical signs or symptoms of illness, and no history of chronic illnesses, were analyzed.

Liver Histology:

The histological diagnosis was established using hematoxylin-eosin and Masson trichrome stains of formalin-fixed paraffin-embedded liver and graded in a blinded fashion by an experienced hepatopathologist (LY) according to the NAFLD scoring system recently proposed by the NIDDK NASH Clinical Research Network. According to this scoring system, the degree of steatosis and inflammatory activity is measured using an 8-point scale (steatosis 0-3; lobular inflammation 0-3; ballooning 0-2). The NAFLD activity score (NAS) is the unweighted sum of steatosis, lobular inflammation and hepatocellular ballooning scores. In accord with the report of the NASH CRN, a NAS of 5 corresponded to a diagnosis of "definitive NASH", 3-4 to "borderline NASH" and <3 to "not NASH". The stage of fibrosis was similarly measured using a 6-point scale (1a, b=mild (1a)/moderate (1b) zone 3 perisinusoidal fibrosis; 1c=portal fibrosis only; 2=zone 3 and portal/periportal fibrosis; 3=bridging fibrosis; 4=cirrhosis).

Immunohistochemistry:

Paraffin embedded liver tissue was cut, deparaffinized and hydrated. Immunohistochemistry was performed by using a mouse monoclonal anti-human M30 antibody (Roche Diagnostics) for detection of caspase cleavage product of CK-18. The samples were incubated with the primary antibody for 1 hour at room temperature diluted 1:50 in the blocking solution. After washing with PBS the sections were incubated with the ready-to-use secondary antibody (DAKO Corporation, Carpinteria, Calif.) for 30 min at room temperature. After washing in PBS, the samples were incubated with a ready-to-use streptavidin-peroxidase conjugate in PBS containing carrier protein and anti-microbial agents (DAKO Corporation, Carpinteria, Calif.) for 30 min at room temperature. After washing with PBS, the samples were stained with 3,3'-diaminobenzidine (DAB, Vector) for 2 to 5 min, washed in PBS, counterstained with hematoxylin for 2 to 3 min, and dehydrated by transferring them through increasing ethanol solutions (30, 50, 70, 80, 95, 100% ethanol). Following dehydration, the slices were soaked twice in a xylene bath at room temperature for 5 min respectively, mounted and examined.

Measurement of Caspase-Generated CK-18 Fragments in the Blood:

A blood sample was obtained from each patient at the time of liver biopsy, processed to plasma and stored frozen at −80° C. The plasma was subsequently used for quantitative measurement of the apoptosis-associated neo-epitope in the C-terminal domain of CK-18 by the M30-Apoptosense ELISA kit (PEVIVA, Alexis, Grunwald, Germany). All assays were performed in triplicate and the absorbance was determined using a microplate reader (Molecular Devices M2, Sunnyvale, Calif., US).

Statistical Analysis:

Descriptive statistics were computed for all variables. These include means and standard deviations or medians, $25^{th}$ and $75^{th}$ percentiles for continuous factors; for categorical variables, frequencies and percentages were estimated. Kruskall-Wallis and Dunn's tests were used to assess if there was any significant differences in terms of continuous clinical or serological characteristics between any of the three subject groups. Chi-square or Fisher's Exact tests were used for categorical factors. Spearman's correlation coefficient was used to estimate the association of plasma CK-18 levels with age, BMI, AST, ALT, AST/ALT ratio, and stage of fibrosis. A logistic regression analysis was used to assess the association between plasma levels of CK-18 fragments and the likelihood of having definitive NASH. Variables that were found to be associated with CK-18 levels in the univariable analysis or those known to be associated with NASH severity (AST/ALT ratio, diabetes, hyperlipidemia, BMI) were studied. To predict the presence of NASH with optimal sensitivity and specificity, receiver operating characteristic (ROC) curve analysis was used to estimate potential cut-off values of plasma CK-18 fragments. A significance level of 0.05 was used for all tests. SAS 9.1 software, SAS Institute, Cary, N.C. and R 2.0.1 software, The R Foundation for Statistical Computing were utilized to perform all analyses.

Results

Patient Characteristics:

The main clinical and serological features of the patients are described in Table 1. Patient's age (50.8±11.1 years), and sex (53.9% females) did not differ significantly between the groups (p=0.76) while BMI was significantly higher in patients with "definitive NASH" as compared to patients with simple steatosis and normal liver biopsies (p<0.001). AST/ALT ratio was not significantly different between the groups (p>0.10). Thirty-one percent had clinical diabetes, 46.2% had hypertension and 46.2% hyperlipidemia (not statistically different between the groups, p>0.15). Thirty-eight percent of patients with a diagnosis of NAFLD had positive autoantibodies (antinuclear, anti-smooth muscle, and/or anti-mitochondrial). Table 2 describes the histological characteristics of the patients: 8 patients (20.5%) had NAS compatible with "not NASH" (simple steatosis), 21 (53.8%) had "definitive NASH". Ten patients (25.6%) with a clinical suspicion of NAFLD had a normal liver biopsy. None of the patients in the normal biopsy and "not NASH" group had fibrosis. Of the 39 subjects, only 2 (5.1%) had cirrhosis; both of which also had "definitive NASH".

TABLE 1

Clinical and Serological characteristics of the patients

| Factor | ALL - N = 39 | Normal Biopsy - N = 10 | Not NASH" (Simple Steatosis) N = 8 | NASH - N = 21 | - P value* |
|---|---|---|---|---|---|
| Age (years) Mean[SD]) | 50.8 (11.1) | 48.9 (7.9) | 46.8 (17.8 | 53.1 (9.0) | NS |
| BMI (Kg/m$^2$) (Means [SD]) | 31.5 (4.0) | 28.6 (2.7) | 31.1 (4.8) | 33.1 (3.6) | 0.008 |
| AST (U/L) ([Median[Q25, Q75]) | 58.0 (46.0, 76.0) | 59.0 (43.0, 66.0) | 50.0 (35.0, 79.5) | 61.0 (46.0, 76.0) | NS |
| ALT (U/L) (Median[Q25, Q75]) | 73.0 (54.0, 104.0) | 78.5 (59.0, 118.0) | 71.0 (47.0, 154.0) | 82.0 (44.0, 101.0) | NS |
| AST/ALT ratio (Mean[SD]) | 0.8 (0.4) | 0.7 (0.2) | 0.8 (0.4) | 0.9 (0.4) | NS |
| Ferritin (Median[Q25, Q75]) | 176.0 (75.6, 397.0) | 75.0 (53.0, 96.0) | 397.0 (53.0, 96.0) | 249.2 (130.4, 485.0) | 0.01 |
| Gender (% Female) | 53.9 | 50 | 50 | 57.1 | NS |
| Race (% Caucasian) | 82.1 | 90 | 62.5 | 85.7 | NS |
| Diabetes % | 30.8 | 20 | 37.5 | 33.3 | NS |
| Hypertension % | 46.2 | 30 | 50 | 52.4 | NS |
| Hyperlipidemia % | 46.2 | 60 | 25 | 47.6 | NS |
| Positive ANA % | 21.6 | 33.3 | 37.5 | 10 | NS |
| Positive SMA % | 26.5 | 11.1 | 42.9 | 27.8 | NS |
| Positive AMA % | 7.4 | 14.3 | 14.3 | 0 | NS |
| Positive Imaging for Fatty Liver % | 62.2 | 20 | 71.4 | 80 | NS |

*P Values correspond the comparison of the three subject groups. Kruskall-Wallis tests for continuous factors or Pearson's chi-square for categorical variables were used.
NOTE:
Positive imaging of fatty liver included ultrasound, CT scan or MRI. Abbreviations: N, number of subjects; AST, aspartate aminotransferase; ALT, alanine aminotransferase; ANA, anti-nuclear antibody; SMA, smooth muscle antibody; AMA, anti-mitochondrial antibody.

TABLE 2

Histological Characteristics of the Patients

| Factor | ALL N = 39 % | Normal Biopsy N = 10 % | "Not NASH" (Simple Steatosis) N = 8 | NASH N = 21 % |
|---|---|---|---|---|
| Steatosis | — | — | — | — |
| <5% | 25.6 | 100 | 0 | 0 |
| 5-33% | 23.1 | 0 | 87.5 | 9.5 |
| 33-66% | 28.2 | 0 | 12.5 | 47.6 |
| >66% | 23.1 | 0 | 0 | 42.9 |
| Lobular Inflammation | — | — | — | — |
| 0-1 | 43.6 | 100 | 87.5 | 0 |
| 2 | 20.5 | 0 | 12.5 | 33.3 |
| 3 | 35.9 | 0 | 0 | 66.7 |
| Ballooning | — | — | — | — |
| 0 | 43.6 | 100 | 87.5 | 0 |
| 1 | 10.3 | 0 | 12.5 | 14.3 |
| 2 | 46.2 | 0 | 0 | 85.7 |
| Fibrosis | — | — | — | — |
| 0 | 53.9 | 100 | 100 | 14.3 |
| 1 | 12.8 | 0 | 0 | 23.8 |
| 2 | 10.3 | 0 | 0 | 19.1 |
| 3 | 18 | 0 | 0 | 33.3 |
| 4 | 51.1 | 0 | 0 | 9.5 |
| Activity Grade | — | — | — | — |
| 0-3 | 46.2 | 100 | 100 | 0 |
| 4-5 | 23.1 | 0 | 0 | 42.9 |
| >5 | 30.8 | 0 | 0 | 57.1 |

NOTE:
Score, grade and activitiy score was determined according to Kleiner et al.
Abbreviation: N, number of subjects Hepatocyte Apoptosis is Increased in Patients with NAFLD and Correlates with Disease Severity.

Figure 2:
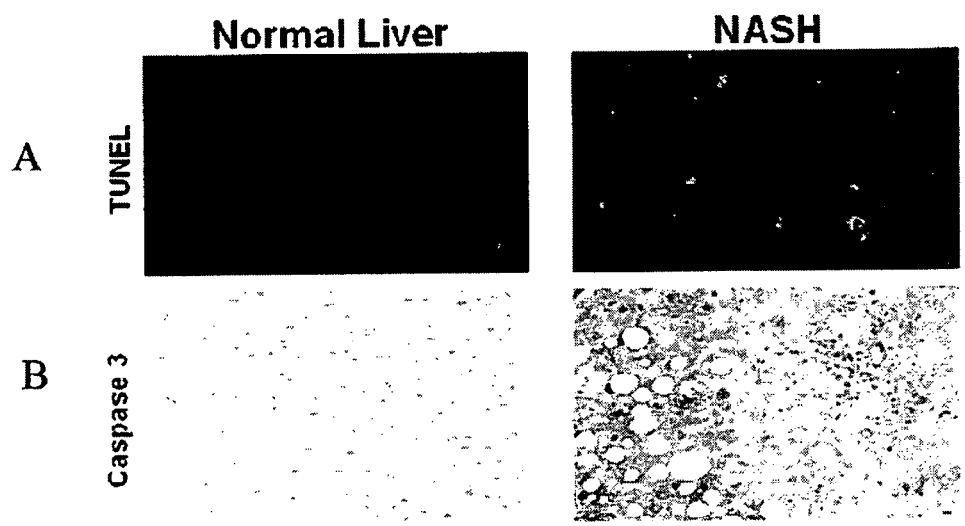
FIG. 2 illustrates hepatocyte apoptosis is increased in Human NASH. Liver sections of patients with NASH (n=34) and of normal liver (n=28) were subjected to (A) TUNEL assay, and (B) immunohistochemistry for activated caspase 3.

Hepatocyte apoptosis was assessed by the TUNEL assay and confirmed by performing immunohistochemistry for activated caspases 3. In liver specimens from control patients, only a few isolated TUNEL-positive cells were identified. In contrast, TUNEL-positive cells were readily observed in liver tissue from patients with NASH (FIG. 2A). Immunohistochemistry for activated caspases 3 was performed using a polyclonal rabbit antibody anti-caspase 3 neoepitope specific antisera (CM1 Ab, IDUN Pharmaceuticals, Inc., La Jolla, Calif.) Immunoreactive product was readily identified in liver tissues from patients with NASH, but was not identified in controls (FIG. 2B).

Hepatocyte Apoptosis is Increased in the Liver of Patients with "Definitive NASH".

Figure 3:
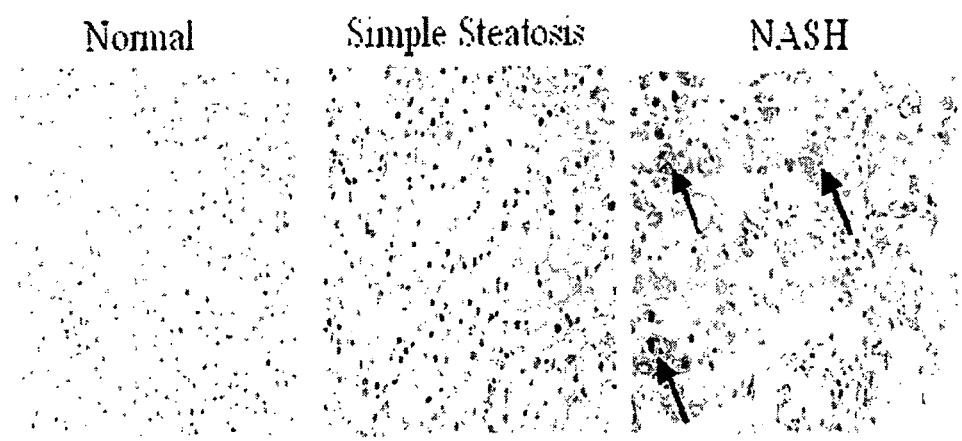
FIG. 3 illustrates caspase 3 generated CK-18 fragments are readily detected in the liver of patients with "definitive" NASH Immunohistochemistry for caspase generated CK-18 fragments was performed in the liver tissue using a mouse monoclonal anti-human antibody (M30) that selectively recognizes the caspase cleavage-generated neo-epitope of CK-18 (original magnification 200×).

Caspase 3 activation and hepatocyte apoptosis have been shown to be prominent features of different experimental models of NAFLD as well as human NAFLD and to correlate with disease severity. To determine whether caspase 3 generated CK-18 are also increased in the liver of NAFLD patients, immunohistochemistry using the M30 monoclonal antibody was performed (FIG. 3). The immunoreactivity product was readily identify in liver tissue from patients with "definitive NASH" but was rarely detected in patients with simple steatosis or those with normal liver biopsies (FIG. 3). These data are consistent with previous studies and confirm the presence of hepatocyte apoptosis in patients with NASH by a complementary and highly specific technique.

Caspase 3-Generated CK-18 Fragments are Markedly Increased in the Blood of Patients with "Definitive NASH".

Figure 4:
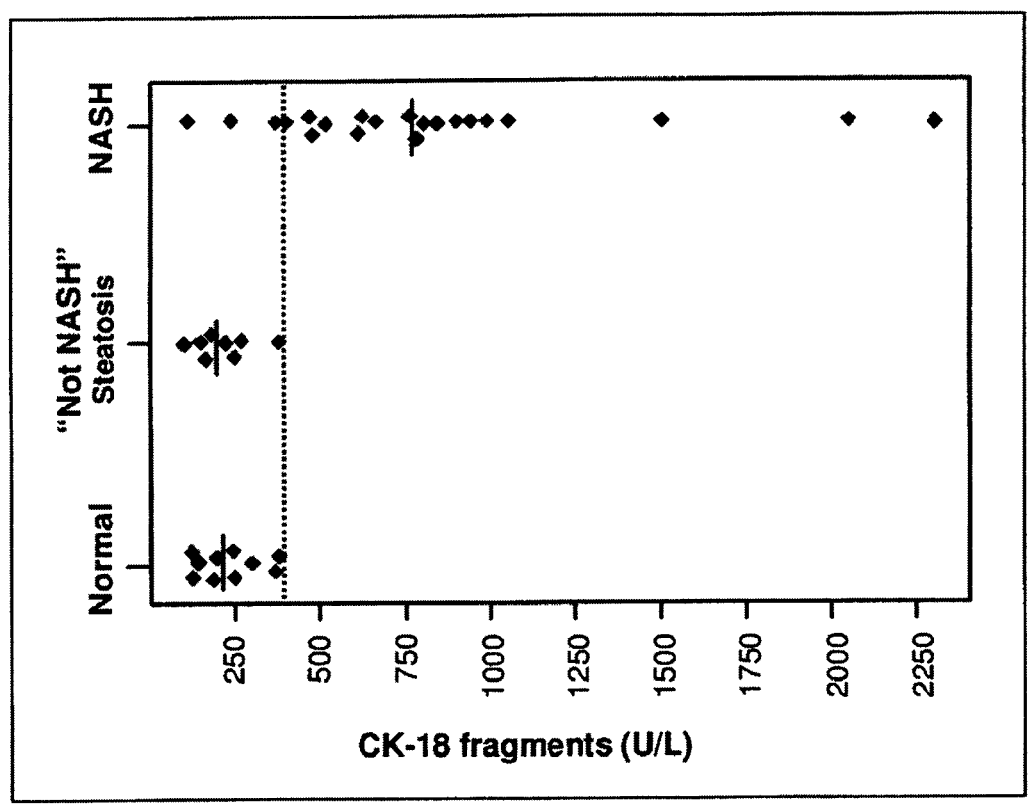
FIG. 4 is a graph illustrating CK-18 fragments are significantly increased in blood of patients with "definitive NASH" compared to patients with δnot NASH" (simple steatosis) as well patients with clinical suspicion of NAFLD but normal biopsy. Median ($25^{th}$, $75^{th}$ percentiles: 766 U/L [480, 991], 202 U/L [160, 258], 215 U/L [150, 296], respectively; P<0.001. A scatter plot of the data is presented with each diamond representing one subject and the solid lines the median values for each group. The dotted line shows the area of overlap between the three groups.

Plasma levels of CK-18 fragments ranged from 105.5 to 2306.4 U/L (median of 516.7 U/L, interquartile range of 246.4 to 804.1 U/L). These levels were significantly higher than those observed in the 35 healthy controls (Median [25th, 75th percentiles]: 234 [197, 289]; p<0.001)". More importantly, CK-18 fragment levels were strikingly higher in patients with "definitive NASH" (NAS of 5) as compared to those with "not NASH" (simple steatosis) or normal biopsies (Median [$25^{th}$, $75^{th}$ percentiles]: 766 U/L [480, 991], 202 U/L [160, 258], 215 U/L [150, 296], respectively; p<0.001) (FIG. 4). Indeed, only 3 patients in the "definitive NASH" group had a CK-18 value that overlapped with the range of the values observed in the other two groups. CK-18 fragment levels showed a weak correlation with body mass index (r=0.36, p=0.024, 95% CI: 0.05, 0.67) and stage of fibrosis (r=0.55, p<0.001, 95% CI: 0.28, 0.82), but not with age (p=0.85), serum AST/ALT ratio (p=0.17), serum AST (p=0.057) or serum ALT (p=0.55). They did not differ significantly according to the presence or absence of history of diabetes, dyslipidemia or hypertension (p>0.30).

Caspase 3-Generated CK-18 Fragments as an Independent Predictor of NASH in Patients with Suspected NAFLD.

Figure 5:
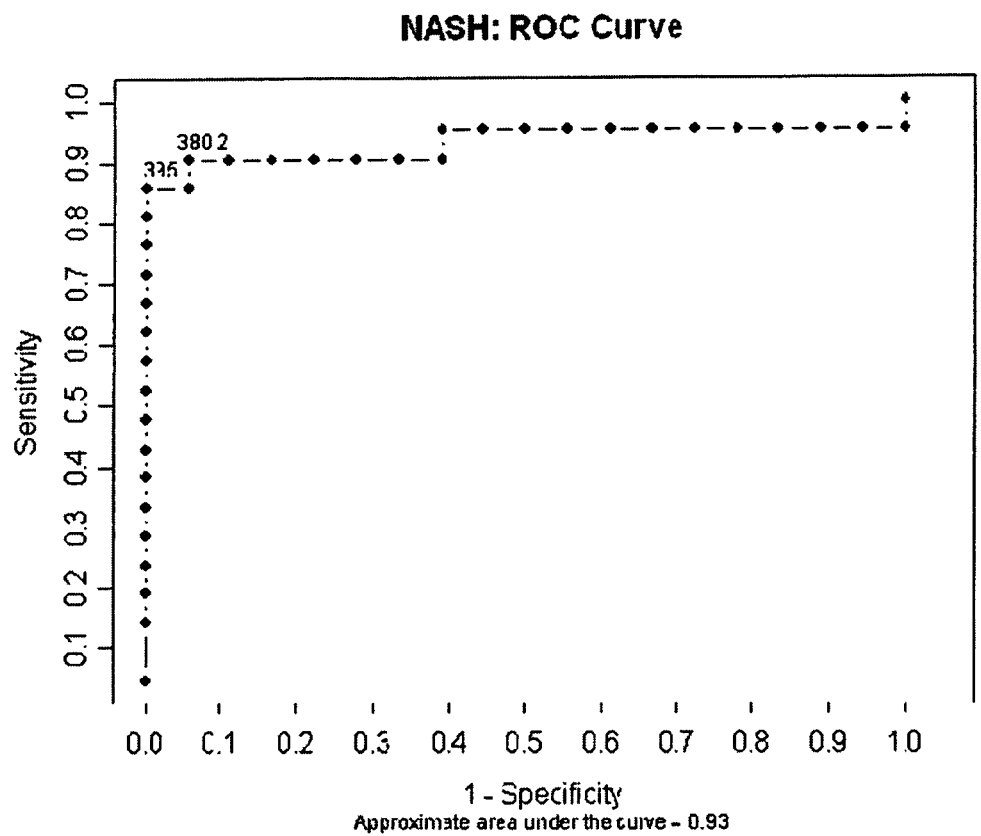
FIG. 5 is a graph illustrating Caspase 3 generated CK-18 fragments accurately predict "definite NASH" in patients with suspected NAFLD. Receiver operating characteristic curve. A cutoff value of 395.0 U/L accurately predicted "definitive NASH" vs. "not NASH" with a specificity of 99.9%, a sensitivity of 85.7% and a positive and negative predictive value of 99.9% and 85.7%, respectively. A value of 380.2 U/L gives a specificity of 94.4%, a sensitivity of 90.5% and a positive and negative predictive value of 95.0% and 89.5%, respectively.

The risk of definitive NASH on liver biopsy increased with increasing plasma levels of caspase 3-generated CK-18 fragments (p=0.019). For every 50 U/L increase in CK-18 levels, the likelihood of having "definitive NASH" increased 86% (OR [95% CI]: 1.86 [1.23, 2.82]). To ascertain whether plasma CK-18 fragment levels independently predicted the presence of "definitive NASH", we used a multivariable logistic regression analysis. Variables associated with CK-18 fragment levels and those that are known to be associated with NASH severity (age, BMI, AST/ALT ratio, diabetes, and hyperlipidemia) were studied as possible confounders of the association between NASH and plasma levels of CK-18 fragments. The adjusted odds ratio of 1.95 and 95% confidence interval (1.18, 3.22) were similar to the unadjusted odds ratio, confirming that elevated levels of CK-18 fragments served as an independent predictor of "definitive NASH" (p<0.05). As none of subjects in the "not NASH" had fibrosis we were unable to adjust for this factor in the multivariable analysis. Using the area under the ROC curve approach we next calculated potential cutoff values to separate patients with "definitive NASH" from those with "not NASH" (FIG. 5). The area under the curve was estimated to be 0.93 (95% CI: 0.83, 1.00) and was found to be significantly higher than 0.5 (chance assignment). Two different cutoff values were calculated (Table 3). The first was selected to minimize the rate of false positive results. Using this approach a cutoff value of 395 U/L accurately predicted "definitive NASH" with a specificity of 99.9%, a sensitivity of 85.7% and positive and negative predictive values of 99.9% and 85.7%, respectively. The second cutoff value was calculated to minimize the false negative rate. In this case a value of 380.2 U/L gave a specificity of 94.4%, a sensitivity of 90.5%, and positive and negative predictive values of 95% and 89.5%, respectively.

TABLE 3

Diagnostic Value of Plasma CK-18 Fragments Determination for Predicting NASH

| | CK-18 Fragment Level Cutoff Value | |
|---|---|---|
| Validity Measures | 395 U/L | 380.2 U/L |
| Specificity (%) | 99.9 | 94.4 |
| Sensitivity (%) | 85.7 | 90.5 |
| PPV (%) | 99.9 | 95.0 |
| NPV (%) | 85.7 | 89.5 |

NOTE:
PPV, positive predictive value; NPV, negative predictive value

Hepatocyte Apoptosis Occurs Early and is a Prominent Pathological Feature in Experimental Models of NAFLD.

Figure 6:
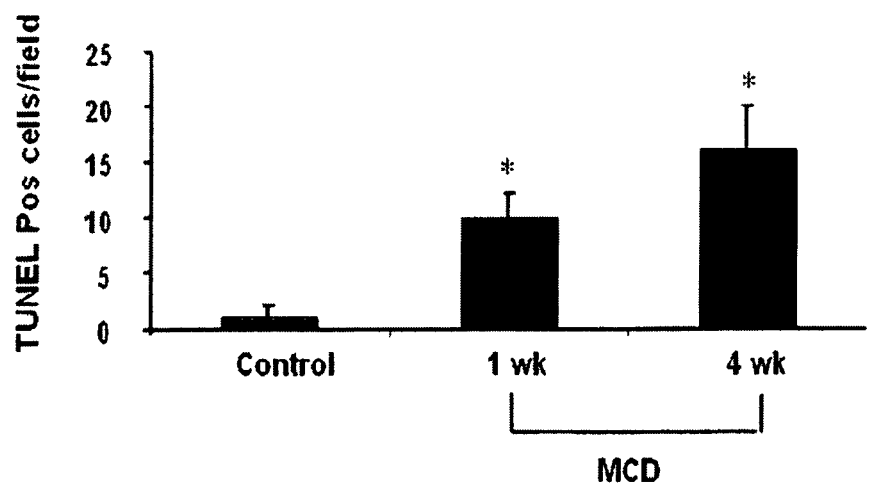
FIG. 6 illustrates hepatocyte apoptosis is increased in diet induced steatohepatitis. C57BL/6 mice were fed a methionine choline deficient (MCD) or control diet ad libidum (n=5 in each group) for 1 or 4 wks. Apoptosis was quantitated using the TUNEL assay (*p<0.001 vs. control).

To investigate the role of hepatocyte apoptosis in the pathogenesis of NAFLD we used a methonine- and choline-deficient diet (MCD), a model of fibrosing steatohepatitis. Experiments were performed after 7 days and 4 wks on either the MCD or control diet. After 7 days on the MCD diet a significant increased in TUNEL positive cells was observed in the MCD fed mice as compared to controls and this was more accentuated following 4 wks on the diet (FIG. 6).

Discussion

NAFLD has been increasingly recognized as one of the most common forms of chronic liver disease affecting up to one third of the US adult population. Natural history data suggest that while patients with simple fatty liver have a relatively benign clinical course, while those with NASH are at particular risk for disease progression and may develop cirrhosis and its complications, including hepatocellular carcinoma. At present, the available non-invasive tests to assess disease severity of NAFLD include clinical signs and symptoms, routine laboratory and radiological imaging tests and combinations of clinical and blood test results. Unfortunately, these tests are of limited utility, and liver biopsy remains the only reliable way of diagnosing NASH and grading the severity of liver damage. There is, therefore, an urgent need to develop and validate novel non-invasive tests that accurately distinguish NASH from simple steatosis and determine the stage and grade of the disease. Such a test would not only aid the clinicians in the selection of patients for liver biopsy but also allow for non-invasive assessment of disease progression and therapeutic response.

Emerging data suggest that hepatocyte apoptosis may be a key component of the "second hit" involved in the progression of simple steatosis to NASH. By using the TUNEL assay and immunohistochemical detection of active caspase 3 in a well-characterized NAFLD patient population, hepatocyte apoptosis has been shown to be a prominent pathologic feature of human NAFLD. Moreover, a positive correlation exists between hepatocyte apoptosis and degree of inflammation and stage of fibrosis. Human and experimental studies in various animal models of NAFLD and in-vitro models of hepatocyte steatosis are now providing further evidence that fat accumulation in liver cells may lead to an increase in apoptotic cell death.

Many forms of apoptosis involve the activation of caspases, which are intracellular proteases that cleave aspartate residues. Indeed, the signature cleavage of proteins after aspartate moieties by caspases is unique to this family of caspases. Furthermore, the cleaved protein generates new epitope(s) for which antibodies can be developed.

We were able to demonstrate that in vivo quantification of hepatocyte apoptosis accurately predicts NASH. Plasma caspase-generated cytokeratin-18 cleavage fragments were strikingly increased in patients with "definitive NASH" as compared to "not NASH" and patients with suspected NAFLD but normal liver biopsy. Moreover, caspase activity levels independently predicted the presence of NASH. Indeed, because of its high sensitivity, specificity, positive and negative predictive value this test has the potential to become an important instrument in clinical practice.

In summary, our findings show that non-invasive monitoring of hepatocyte apoptosis in blood of patients with NAFLD is a novel and reliable tool to differentiate NASH from "not NASH" in patients with suspected NAFLD.

EXAMPLE 2

CK-18 Levels as a Diagnostic Test for NASH in Patients Who have Undergone Bariatric Surgery This example presents the results of a study regarding CK-18 levels in patients who have undergone bariatric surgery.

Aims.

To assess the utility of CK-18 levels in the diagnosis of NASH and fibrosis in patients who have undergone bariatric surgery.

Data.

Histological data was available for a total of 99 subjects. Of these, 86 also had CK-18 levels measured. Fibrosis could not be assessed for 1 subject.

Statistical Analysis.

Descriptive statistics were computed for all variables. These include means and standard deviations or medians, as well as 25th and 75th percentiles for continuous factors. For categorical variables, frequencies and percentages were estimated. Kruskal-Wallis and Dunn's tests were used to assess whether CK-18 levels were significantly different between the three subject groups. In addition, Wilcoxon rank sum tests were used to compare CK-18 levels between subjects with moderate to severe fibrosis and those with mild fibrosis; the same was done for presence of fibrosis. Spearman's correlation coefficients were used to assess associations between CK-18 levels and histological characteristics. Logistic regression analysis was used to assess the association between plasma levels of CK-18 fragments and the likelihood of having definitive NASH as opposed to simple steatosis. To predict the presence of NASH with optimal sensitivity and specificity, receiver operating characteristic curve analysis was used to estimate potential cutoff values of plasma CK-18 fragments. The same was done to assess the utility of CK-18 levels in the prediction of fibrosis. A P value of 0.05 was considered statistically significant. SAS version 9.1 software (SAS Institute, Cary, N.C.) and R 2.0.1 software (The R Foundation for Statistical Computing) were used to perform all analyses.

Results.

Descriptive statistics for histological characteristics by NAFLD diagnosis are presented on Table 4.

Table 5 present descriptive statistics for CK-18 fragment levels by subject group and fibrosis grade. CK-18 levels ranged from 103 to 1000 U/L (median (Q25, Q75):226 (177, 298)).

Compared to either subjects with no NAFLD, simple steatosis or borderline diagnosis, CK-18 levels were significantly higher in subjects with NASH (median (Q25, Q75): 196 (158, 245) vs. 217 (154, 228) vs. 200 (176, 274) vs. 389 (275, 839), respectively; P<0.0001). On the other hand, there was no evidence to suggest a difference in CK-18 levels between subjects without NAFLD, and those with simple steatosis or a borderline diagnosis (P>0.40).

Although the correlation between fibrosis grade and CK-18 level was found to be weak (r (95% CI): 0.27 (0.06, 0.48)), levels were significantly higher in subjects with moderate to severe fibrosis than in those with mild fibrosis (median (Q25, Q75): 334.5 (240.5, 896) vs. 207 (175, 275), respectively; P=0.007)).

Table 6 presents descriptive statistics for the association between CK-18 levels and histological characteristics.

Prediction of NASH Based on CK-18 Levels

For every 50 U/L increase in the plasma level of CK-18, the likelihood of having NASH as opposed to simple steatosis increases 2.45 times (OR (95% CI): 2.45 (1.20, 5.00)). The area under the ROC curve was estimated to be 0.88 (95% CI: 0.77, 0.99) and was found to be significantly higher than 0.5 (i.e. better than chance assignment). The value with the best combination of sensitivity and specificity are 252 U/L (sensitivity=81.8% and specificity=76.9%) and 275 U/L (sensitivity=77.3% and specificity=100%).

Prediction of Fibrosis Based on CK-18 Levels Moderate to Severe Fibrosis.

For every 50 U/L increase in the plasma level of CK-18, the likelihood of having fibrosis increases 18% (OR (95% CI): 1.18 (1.06, 1.32)).

The area under the ROC curve was estimated to be 0.75 (95% CI: 0.60, 0.91) and was found to be significantly higher than 0.5. The value with the best combination of sensitivity and specificity are 252 U/L (sensitivity=75% and specificity=67.1%) and 275 U/L (sensitivity=66.7% and specificity=74.0%).

TABLE 4

Histological Characteristics

| Factor | ALL (N = 86) | No NAFLD (N = 21) | Steatosis (N = 13) | Borderline (N = 30) | NASH (N = 22) |
|---|---|---|---|---|---|
| Steatosis | | | | | |
| <5% | 31 (36.1) | 21 (100.0) | 9 (69.2) | 1 (3.3) | 0 (0.0) |
| 5-33% | 30 (34.9) | 0 (0.0) | 4 (30.8) | 24 (80.0) | 2 (9.1) |
| 34-65% | 14 (16.3) | 0 (0.0) | 0 (0.0) | 4 (13.3) | 10 (45.5) |
| >=66% | 11 (12.8) | 0 (0.0) | 0 (0.0) | 1 (3.3) | 10 (45.5) |
| Lobular Inflammation | | | | | |
| None | 34 (39.5) | 21 (100.0) | 9 (69.2) | 3 (10.0) | 1 (4.6) |
| <2 under 20x | 36 (41.9) | 0 (0.0) | 4 (30.8) | 26 (86.7) | 6 (27.3) |
| 2-4 under 20x | 16 (18.6) | 0 (0.0) | 0 (0.0) | 1 (3.3) | 15 (68.2) |
| Ballooning | | | | | |
| None | 28 (32.6) | 21 (100.0) | 5 (38.5) | 2 (6.7) | 0 (0.0) |
| Few | 22 (25.6) | 0 (0.0) | 8 (61.5) | 13 (43.3) | 1 (4.6) |
| Many | 36 (41.9) | 0 (0.0) | 0 (0.0) | 15 (50.0) | 21 (95.5) |
| Fibrosis* | | | | | |
| 0 | 51 (60.7) | 20 (95.2) | 10 (90.9) | 15 (50.0) | 6 (27.3) |
| 1 | 21 (25.0) | 1 (4.8) | 1 (9.1) | 12 (40.0) | 7 (31.8) |
| 2 | 9 (10.7) | 0 (0.0) | 0 (0.0) | 3 (10.0) | 6 (27.3) |
| 3 | 3 (3.6) | 0 (0.0) | 0 (0.0) | 0 (0.0) | 3 (13.6) |
| NAS | | | | | |
| 0 | 21 (24.4) | 21 (100.0) | 0 (0.0) | 0 (0.0) | 0 (0.0) |
| 1 | 10 (11.6) | 0 (0.0) | 10 (76.9) | 0 (0.0) | 0 (0.0) |
| 2 | 3 (3.5) | 0 (0.0) | 3 (23.1) | 0 (0.0) | 0 (0.0) |
| 3 | 14 (16.3) | 0 (0.0) | 0 (0.0) | 14 (46.7) | 0 (0.0) |
| 4 | 16 (18.6) | 0 (0.0) | 0 (0.0) | 16 (53.3) | 0 (0.0) |
| 5 | 9 (10.5) | 0 (0.0) | 0 (0.0) | 0 (0.0) | 9 (40.9) |
| 6 | 5 (5.8) | 0 (0.0) | 0 (0.0) | 0 (0.0) | 5 (22.7) |
| 7 | 8 (9.3) | 0 (0.0) | 0 (0.0) | 0 (0.0) | 8 (36.4) |

Values presented are N (%)
*Fibrosis could not be assessed for one subject with steatosis

TABLE 5

CK-18 Levels by Diagnosis and Fibrosis

| Factor | N | Median (Q25, Q75) | P Value |
|---|---|---|---|
| Group | | | |
| No NAFLD | 21 | 196 (158, 245) | |
| Simple Steatosis | 13 | 217 (154, 228) | <0.0001 |
| Borderline | 30 | 200 (176, 274) | |
| NASH | 22 | 389 (275, 839) | |
| Fibrosis | | | |
| Mild | 73 | 207 (175, 275) | |
| Moderate/Severe Fibrosis | 12 | 334.5 (240.5, 896) | 0.007 |
| No | 51 | 206 (173,271) | |
| Yes | 34 | 263.5 (182, 383) | 0.053 |

TABLE 6

Correlation Between CK-18 Levels and Histological Characteristics

| Factor | rho | 95% CI | P value |
|---|---|---|---|
| NAS | 0.44 | (0.24, 0.63) | <0.001 |
| Steatosis | 0.4 | (0.20, 0.60) | <0.001 |
| Lobular Inflammation | 0.45 | (0.25, 0.64) | <0.001 |
| Ballooning | 0.33 | (0.12, 0.53) | 0.002 |
| Fibrosis | 0.27 | (0.06, 0.48) | 0.013 |

Having described the invention the following is claimed:

1. A method of assessing the degree of liver damage associated with non-alcoholic fatty liver disease in a subject with non-alcoholic fatty liver disease, the method comprising:
    obtaining a bodily sample from the subject, wherein the bodily sample is selected from the group consisting of blood, plasma, and serum;
    measuring the level of caspase generated cytokeratin-18 fragments in the bodily sample;
    correlating the level of caspase generated cytokeratin-18 fragments with the degree of liver damage in the subject;
    identifying the subject as having more severe liver damage the higher the measured level of caspase generated cytokeratin-18 fragments in the bodily sample compared to a predetermined value; and
    administering to the subject having non-alcoholic fatty liver disease a therapeutic agent based on the identified severity of liver damage.

2. The method of claim 1, the caspase generated cytokeratin-18 fragments being measured using an enzyme-linked immunosorbent assay (ELISA).

3. The method of claim 2, the enzyme-linked immunosorbent assay measuring the level of caspase generated cytokeratin-18 fragments in units per liter (U/L), wherein the higher the U/L of caspase generated cytokeratin-18 fragments in the bodily sample the more severe the liver damage in the subject.

4. The method of claim 1, wherein the higher the measured level of caspase generated cytokeratin-18 fragments in the bodily sample compared to a predetermined value, the more likely the subject has nonalcoholic steatohepatitis (NASH) than steatosis.

5. The method of claims 1, wherein the higher the measured level of caspase generated cytokeratin-18 fragments in the bodily sample compared to a predetermined value, the more likely the subject has moderate to severe fibrosis than mild fibrosis.

6. The method of claim 1, wherein a level of caspase generated cytokeratin-18 fragments are measured in the bodily sample and the level of caspase generated cytokeratin-18 fragments are correlated with the degree of liver damage in the subject, wherein the higher the measured level of caspase generated cytokeratin-18 fragments in the bodily sample compared to a predetermined value, the more severe the liver damage in the subject.

7. The method of claim 1, wherein a level of caspase generated cytokeratin-18 fragments which are cleaved at aspartic acid residue 396 are measured in the bodily sample and the level of caspase generated cytokeratin-18 fragments which are cleaved at aspartic acid residue 396 are correlated with the degree of liver damage in the subject, wherein the higher the measured level of caspase generated cytokeratin-18 fragments which are cleaved at aspartic acid residue 396 in the bodily sample compared to a predetermined value, the more severe the liver damage in the subject.

8. The method of claim 1, wherein a level of caspase generated cytokeratin-18 fragments which are cleaved at aspartic acid residue 396 are measured in the bodily sample and the level of caspase generated cytokeratin-18 fragments which are cleaved at aspartic acid residue 396 are correlated with the degree of liver damage in the subject, wherein the higher the measured level of caspase generated cytokeratin-18 fragments which are cleaved at aspartic acid residue 396 in the bodily sample compared to a predetermined value, the more severe the liver damage in the subject.

9. A method of assessing the degree of liver damage associated with non-alcoholic fatty liver disease in a subject with non-alcoholic fatty liver disease, the method comprising:
obtaining a bodily sample from the subject, wherein the bodily sample is selected from the group consisting of blood, plasma, and serum;
measuring the level of cytokeratin-18 fragments which are cleaved at aspartic acid residue 396 in the bodily sample;
correlating the level of cytokeratin-18 fragments which are cleaved at aspartic acid residue 396 with the degree of liver damage in the subject;
identifying the subject as having more severe liver damage the higher the measured level of cytokeratin-18 fragments which are cleaved at aspartic acid residue 396 in the bodily sample compared to a predetermined value; and
administering to the subject having non-alcoholic fatty liver disease a therapeutic agent based on the identified severity of liver damage.

10. The method of claim 9, the cytokeratin-18 fragments being measured using an enzyme-linked immunosorbent assay (ELISA).

11. The method of claim 10, the enzyme-linked immunosorbent assay measuring the level of cytokeratin-18 fragments which are cleaved at aspartic acid residue 396 in units per liter (U/L), wherein the higher the U/L of cytokeratin-18 fragments which are cleaved at aspartic acid residue 396 in the bodily sample the more severe the liver damage in the subject.

12. The method of claim 9, wherein the higher the measured level of cytokeratin-18 fragments which are cleaved at aspartic acid residue 396 in the bodily sample compared to a predetermined value, the more likely the subject has nonalcoholic steatohepatitis (NASH) than steatosis.

13. The method of claims 9, wherein the higher the measured level of cytokeratin-18 fragments which are cleaved at aspartic acid residue 396 in the bodily sample compared to a predetermined value, the more likely the subject has moderate to severe fibrosis than mild fibrosis.

14. A method of assessing the degree of liver damage associated with non-alcoholic fatty liver disease in a subject with non-alcoholic fatty liver disease, the method comprising:
obtaining a bodily sample from the subject, wherein the bodily sample is selected from the group consisting of blood, plasma, and serum;
measuring the level of caspase generated cytokeratin-18 fragments which are cleaved at aspartic acid residue 396 in the bodily sample;
correlating the level of caspase generated cytokeratin-18 fragments which are cleaved at aspartic acid residue 396 with the degree of liver damage in the subject;
identifying the subject as having more severe liver damage the higher the measured level of caspase generated cytokeratin-18 fragments which are cleaved at aspartic acid residue 396 in the bodily sample compared to a predetermined value; and
administering to the subject having non-alcoholic fatty liver disease a therapeutic agent based on the identified severity of liver damage.

15. The method of claim 14, the caspase generated cytokeratin-18 fragments being measured using an enzyme-linked immunosorbent assay (ELISA).

16. The method of claim 15, the enzyme-linked immunosorbent assay measuring the level of caspase generated cytokeratin-18 fragments which are cleaved at aspartic acid residue 396 in units per liter (U/L), wherein the higher the U/L of caspase generated cytokeratin-18 fragments which are cleaved at aspartic acid residue 396 in the bodily sample the more severe the liver damage in the subject.

17. The method of claim 14, wherein the higher the measured level of caspase generated cytokeratin-18 fragments which are cleaved at aspartic acid residue 396 in the bodily sample compared to a predetermined value, the more likely the subject has nonalcoholic steatohepatitis (NASH) than steatosis.

18. The method of claims 14, wherein the higher the measured level of caspase generated cytokeratin-18 fragments which are cleaved at aspartic acid residue 396 in the bodily sample compared to a predetermined value, the more likely the subject has moderate to severe fibrosis than mild fibrosis.

* * * * *